United States Patent
Rho et al.

(10) Patent No.: US 12,239,668 B2
(45) Date of Patent: Mar. 4, 2025

(54) PHARMACEUTICAL COMPOSITION COMPRISING PERIODONTAL TISSUE-DERIVED PLURIPOTENT STEM CELLS FOR PREVENTION OR TREATMENT OF MALE INFERTILITY

(71) Applicants: INDUSTRY-ACADEMIC COOPERATION FOUNDATION GYEONGSANG NATIONAL UNIVERSITY, Jinju-si (KR); STEMCENTRIC CO., LTD., Anyang-si (KR)

(72) Inventors: Gyu Jin Rho, Jinju si (KR); Kyung Min Kim, Seoul (KR); Si Jung Jang, Jinji si (KR); Sung Lim Lee, Jinju si (KR); Bong Wook Park, Jinju si (KR)

(73) Assignees: Industry-Academic Cooperation Foundation Gyeongsang National University (KR); Stemcentric Co., Ltd. (KR)

( * ) Notice: Subject to any disclaimer, the term of this patent is extended or adjusted under 35 U.S.C. 154(b) by 715 days.

(21) Appl. No.: 17/609,460

(22) PCT Filed: May 8, 2020

(86) PCT No.: PCT/KR2020/006091
§ 371 (c)(1),
(2) Date: Nov. 8, 2021

(87) PCT Pub. No.: WO2020/226451
PCT Pub. Date: Nov. 12, 2020

(65) Prior Publication Data
US 2022/0226385 A1     Jul. 21, 2022

(30) Foreign Application Priority Data
May 8, 2019 (KR) .......................... 10-2019-0053424

(51) Int. Cl.
*A61K 35/12* (2015.01)
*A61K 35/28* (2015.01)
(Continued)

(52) U.S. Cl.
CPC .............. *A61K 35/28* (2013.01); *A61K 35/32* (2013.01); *A61P 5/24* (2018.01)

(58) Field of Classification Search
CPC ..................................................... A61K 35/12
See application file for complete search history.

(56) References Cited

U.S. PATENT DOCUMENTS

| | | |
|---|---|---|
| 8,980,847 B2 | 3/2015 | Kim et al. |
| 2018/0055887 A1 | 3/2018 | Lu et al. |

FOREIGN PATENT DOCUMENTS

| | | |
|---|---|---|
| JP | 2006-115837 A | 5/2006 |
| KR | 10-2013-0035091 A | 4/2013 |

(Continued)

OTHER PUBLICATIONS

English translation of Hokkaido University, WO 2019/074046 A1, Apr. 2019.*

(Continued)

*Primary Examiner* — Rosanne Kosson
(74) *Attorney, Agent, or Firm* — POLSINELLI PC (57) ABSTRACT

The present invention relates to a pharmaceutical composition including vitrified periodontal tissue-derived mesenchymal stem cells for prevention or treatment of male infertility. The pharmaceutical composition for prevention or treatment of male infertility according to the present invention recovers sex hormone levels in seminiferous tubules of atrophic testes and blood to normal levels through improvement in the activity of lipid metabolism enzymes in the liver, thereby exhibiting remarkable prophylactic and therapeutic effects on male infertility. In addition, the periodontal tissue-de- (Continued)

rived mesenchymal stem cells which are an active ingredient in the present invention can be obtained in the most non-invasive manner and as such, are expected to be advantageously used as a cell therapy product for male infertility.

6 Claims, 7 Drawing Sheets

(51) Int. Cl.
*A61K 35/32* (2015.01)
*A61P 5/24* (2006.01)

(56) References Cited

FOREIGN PATENT DOCUMENTS

| KR | 10-2015-0069469 A | 6/2015 | |
|---|---|---|---|
| KR | 10-1551900 B1 | 6/2015 | |
| WO | WO-2019074046 A1 * | 4/2019 | ............. A61K 35/32 |

OTHER PUBLICATIONS

Dave et al., "Dental tissue-derived mesenchymal stem cells: applications in tissue engineering," Critical Reviews in Biomedical Engineering 46(5):429-468, 2018.*
Hassan et al., "Evaluation of mesenchymal stem cells in treatment of infertility in male rats," Stem Cell Research & Therapy 2014, 5: 131, 15 pages.
International Search Report and Written Opinion, PCT/KR2020/006091, Sep. 8, 2020, 9 pages.

* cited by examiner

PHARMACEUTICAL COMPOSITION COMPRISING PERIODONTAL TISSUE-DERIVED PLURIPOTENT STEM CELLS FOR PREVENTION OR TREATMENT OF MALE INFERTILITY

CROSS-REFERENCE TO RELATED APPLICATIONS

This application is U.S. national phase application under 35 U.S.C. § 371 of International Application No. PCT/KR2020/006091, filed on May 8, 2020, which claims the benefit of priority to Korean Patent Application No. KR10-2019-0053424, filed on May 8, 2019, and the contents of each of which are incorporated herein by reference in their entirety.

TECHNICAL FIELD

The present invention relates to a pharmaceutical composition containing vitrified periodontal tissue-derived mesenchymal stem cells for prevention or treatment of male infertility.

BACKGROUND ART

The number of male infertility patients has increased rapidly over the past four years, increasing about 1.5 times from 43,094 in 2013 to 62,468 in 2017. As of 2012, the number of males aged 35 to 39 who had undergone infertility treatment per year was 695 per 100,000 of population and the number of males aged 40 to 44 was 266 per 100,000. In a gender comparison over the past five years, the number of female infertility patients has increased by an average of 2.5% per year, while the number of male infertility patients has rapidly increased by 11.8% per year.

Male infertility is caused by various factors, including hormonal problems including male hormones, testicular problems due to exposure to toxic substances, infection, and trauma, problems with sperm, and abnormal passageways of sperm release. Recently, it has been reported that male infertility shows a higher than average increase rate in relation to modern lifestyles such as obesity, diabetes, smoking and stress. Obesity was overlooked until early 2010, and as a pathological association with infertility has been reported, it has recently attracted attention as a factor directly related to infertility among numerous factors of infertility. A series of studies have been reported that in obese men, excessive adipose tissue causes problems in the metabolism of sex hormones, which changes the male hormone (testosterone) to the female hormone (estrogen) and interferes with sperm production, and excess fat in obese men raises body temperature, and thus sperm cannot be produced well. In addition, non-alcoholic fatty liver disease (NAFLD) is the most common chronic liver disease, and the main cause is known to be obesity. NAFLD causes sex hormone imbalance due to hepatocyte damage, leading to chronic male infertility such as male hypogonadism. In particular, since most estrogen is metabolized in the liver tissue, damage to hepatocytes causes a problem in the estrogen removal system, which has been proven by studies that sex hormone imbalance due to liver cirrhosis is improved after liver transplantation.

As for male infertility, which is related to obesity, liver disease, and the like, hormone therapy, and various drugs that can affect spermatogenic function are used, such as kallikrein, carnitine, pentoxifylline, nonsteroidal anti-inflammatory drugs, and alpha blockers. In the case of hormone therapy such as testosterone replacement therapy (TRT), the clinical success rate is inconsistent or fatal side effects are reported. In the case of non-hormone therapy, the exact standard of action of a drug is often unknown. In addition, it is known that there is no effective treatment method for hypogonadism. Accordingly, there is a need for new therapies that can fundamentally treat chronic male infertility due to hepatocyte damage caused by obesity and NAFLD.

Periodontal tissue-derived mesenchymal stem cells are a type of mesenchymal stem cells. According to recent studies, it has been found that mesenchymal stem cells can differentiate not only into mesoderm but also into ectoderm (mainly nerve cells) or endoderm (hepatocytes, pancreatic cells, etc.), and are recognized as having multipotency.

DISCLOSURE

Technical Problem

Accordingly, the present inventors have tried to develop a new therapeutic agent that can replace male infertility treatment, which has many side effects reported, and as a result, the present inventors found that when vitrified periodontal tissue-derived mesenchymal stem cells were administered to an animal model of infertility through a high-fat diet, sex hormone levels in seminiferous tubules of testes and blood were recovered to levels similar to those of normal models, thereby being effective against male infertility, and then completed the present invention.

Accordingly, an aspect of the present invention is directed to providing a pharmaceutical composition containing periodontal tissue-derived mesenchymal stem cells for prevention or treatment of male infertility.

Another aspect of the present invention is directed to providing a stem cell therapeutic agent containing periodontal tissue-derived mesenchymal stem cells for treatment of male infertility.

Technical Solution

In order to achieve the above purpose, the present invention provides a pharmaceutical composition containing periodontal tissue-derived mesenchymal stem cells for prevention or treatment of male infertility.

In addition, the present invention provides a stem cell therapeutic agent containing periodontal tissue-derived mesenchymal stem cells for treatment of male infertility.

In addition, the present invention provides a method for treatment of male infertility, in which the method includes treating a subject with periodontal tissue-derived mesenchymal stem cells.

Advantageous Effects

The pharmaceutical composition for prevention or treatment of male infertility according to the present invention recovers sex hormone levels in seminiferous tubules of atrophic testes and blood to normal levels through improvement in the activity of lipid metabolism enzymes in the liver, thereby exhibiting remarkable prophylactic and therapeutic effects on male infertility. In addition, the periodontal tissue-derived mesenchymal stem cells which are an active ingredient in the present invention can be obtained in the most non-invasive manner and as such, are expected to be advantageously used as a cell therapeutic agent for male infertility.

MODES OF THE INVENTION

The present invention provides a pharmaceutical composition containing periodontal tissue-derived mesenchymal stem cells for prevention or treatment of male infertility.

Hereinafter, the present invention will be described in detail.

Terms not otherwise defined herein have the meanings commonly used in the technical field to which the present invention pertains.

As used herein, the term "stem cells" is a generic term for undifferentiated cells before differentiation into respective cells constituting tissue, and the stem cells have an ability to be differentiated into particular cells by particular differentiation stimulations (environment).

As used herein, the term "mesenchymal stem cells (MSCs)" is also referred to as mesenchymal stem cells or adult stem cells, and commonly refers to stem cells isolated and cultured from tissues other than embryos. Mesenchymal stem cells are present in small amounts in most tissues that have already been differentiated, and their presence has been identified in almost all tissues studied so far, such as umbilical cord blood, umbilical cord, teeth, eyes, placenta, hair follicles, lungs, and liver.

As used herein, the term "periodontal tissue-derived mesenchymal stem cells" includes both adult stem cells derived from teeth and periodontal tissue and cells similar in morphology to mesenchymal stem cells (mesenchymal stem cell-like cells). The periodontal tissue-derived mesenchymal stem cells have the advantage of minimizing tissue damage and being easily obtainable (non-invasively) compared to other adult stem cells present in the bone marrow or umbilical cord, and thus were used as an active ingredient of the present invention. The periodontal tissue is not limited thereto, but may be pulp tissue of primary or permanent teeth, periodontal ligament tissue, dental follicle tissue of erupting teeth, dental germ stem tissue, and root papillary tissue of immature permanent teeth, preferably wisdom teeth surrounding tissue.

In addition, the tissue may contain mesenchymal stem cells, in which the mesenchymal stem cells may be one or more selected from the group consisting of dental pulp stem cells (DPSCs), stem cells from human exfoliated deciduous teeth (SHEDs), periodontal ligament stem cells (PDLSCs), dental follicle stem cells (DFSCs), and stem cells from apical papilla (SCAP), but are not limited thereto.

Such periodontal tissue-derived mesenchymal stem cells have been clinically applied to regenerative medicine to treat or improve peri-implantitis, nerve damage, and loss of gingival bone. However, so far, there have been no reports of any medical effects on male infertility.

In the present invention, the periodontal tissue is isolated from the human body and vitrified, and the vitrification method may use a method described in Korean Patent No. 10-1551900 (Patent Document 1), which is a related art of the present inventors.

In the present invention, as a method for isolating mesenchymal stem cells, methods known in the pertinent art may be used without limitation. For example, the mesenchymal stem cells may be isolated and purified from periodontal tissue, and the isolated mesenchymal stem cells may be cultured if necessary.

In the present invention, the male infertility is not limited thereto, but may be caused by obesity, diabetes, smoking, stress and non-alcoholic fatty liver disease, preferably obesity or non-alcoholic fatty liver disease (NAFLD).

In the present invention, the "pharmaceutical composition containing periodontal tissue-derived mesenchymal stem cells for prevention or treatment of male infertility" may be periodontal tissue-derived mesenchymal stem cells themselves, and include a composition containing a culture medium, and a substance generally used in the pertinent art when culturing stem cells, in addition to periodontal tissue-derived mesenchymal stem cells. In addition, it is meant to include a use of a substance secreted by periodontal tissue-derived mesenchymal stem cells or a substance extracted from periodontal tissue-derived mesenchymal stem cells in place of periodontal tissue-derived mesenchymal stem cells.

In the present invention, the pharmaceutical composition may include a pharmaceutically acceptable carrier, in addition to periodontal tissue-derived mesenchymal stem cells. For injection, the formulation may include a preservative, an analgesic, a solubilizer, a stabilizer or the like, and for topical administration, the formulation may include a base, an excipient, a lubricant, a preservative or the like.

A pharmaceutically acceptable carrier contained in the pharmaceutical composition of the present invention is typically used in the formulation. Examples thereof include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrups, methyl cellulose, methylhydroxybenzoate, propylhydroxybenzoate, talc, magnesium stearate, and mineral oil, but are not limited thereto. The pharmaceutical composition of the present invention may further include lubricants, wetting agents, sweeteners, aromatics, emulsifiers, suspensions, and preservatives besides the above components.

The pharmaceutical composition of the present invention may be prepared in a unit dosage form or enclosed in a multi-dose container using a pharmaceutically acceptable carrier and/or excipient according to a method easily carried out by a skilled having ordinary skill in the technical field to which the present invention pertains. Herein, the formulation may be a solution in oil or an aqueous medium, suspension, or emulsion, and may further include a dispersing agent or a stabilizing agent.

The pharmaceutical composition of the present invention may be administered parenterally (for example, intravenously, subcutaneously, intraperitoneally, or topically). The composition for parenteral administration (for example, injectable solution) according to the present invention may be injected in vivo by dispersion and/or dissolution thereof in a pharmaceutically acceptable carrier, for example, sterile purified water, a buffer of about pH 7, or saline solution. The pharmaceutical composition may include a conventional additive such as a preservative, a stabilizer or the like, if necessary.

In addition, in the present invention, the amount of mesenchymal stem cells may be injected in an amount of $10^4$ to $10^{10}$ cells/injection, preferably $10^5$ to $10^9$ cells/injection, more preferably $10^6$ to $10^8$ cells/injection, and most preferably $5 \times 10^7$ to $10^8$ cells/injection, but is not limited thereto. The dosage may be prescribed in various ways depending on factors such as a formulation method, an administration method, the age, weight, and pathosis of a patient, food, administration time, an administration route, an excretion rate, and sensitivity to reaction.

The pharmaceutical composition of the present invention may be administered one or more times, preferably administered three or more times at an interval of 1 to 3 weeks, and most preferably administered three or more times at an interval of 2 weeks.

In the present invention, the pharmaceutical composition may improve atrophy of seminiferous tubules in a testicle, and may improve sex hormone imbalance due to liver damage.

In example of the present invention, it was identified that when the periodontal tissue-derived mesenchymal stem cells were administered, the testicular structure of the male infertility animal model was recovered and the seminiferous tubules were improved, such as the formation of sperm in the lumen. It was identified that as the diameter length increased, the histological characteristics of the seminiferous tubules were remarkably recovered, and the number of Leydig cells producing testosterone significantly increased.

In addition, in another example of the present invention, it was identified that as the periodontal tissue-derived mesenchymal stem cells were administered, the testosterone/17β-estradiol value corresponding to the clinical indicator of the serum testosterone level and sex hormone balance increased, so that the sex hormone imbalance according to the high-fat diet (obesity) was significantly improved.

The pharmaceutical composition of the present invention may be used alone or in combination with methods for preventing or treating male infertility known in the pertinent art for the prevention and treatment of male infertility.

In addition, the present invention provides a stem cell therapeutic agent containing periodontal tissue-derived mesenchymal stem cells for treatment of male infertility.

In the present invention, the periodontal tissue is not limited thereto, but may be pulp tissue of primary or permanent teeth, periodontal ligament tissue, dental follicle tissue of erupting teeth, dental germ stem tissue, and root papillary tissue of immature permanent teeth, preferably wisdom teeth surrounding tissue.

As used herein, the term "cell therapeutic agent" refers to a drug used for the purpose of treatment, diagnosis and prevention, which contains a cell or tissue prepared through isolation from a human being, culture and specific operation (as provided by the US FDA), and refers to a drug used for the purpose of treatment, diagnosis and prevention through a series of behaviors of in vitro proliferating and sorting living autologous, allogenic and xenogenic cells or changing the biological characteristics of cells by other means for the purpose of recovering the functions of cells or tissues.

As used herein, the term "prevention" refers to all actions that inhibit male infertility or delay the progression of male infertility by administration of a pharmaceutical composition or a stem cell therapeutic agent according to the present invention.

As used herein, the term "treatment" refers to all actions that alleviate or beneficially change male infertility by administration of a pharmaceutical composition or a stem cell therapeutic agent according to the present invention.

In addition, the present invention provides a method for treatment of male infertility, in which the method includes treating a subject with periodontal tissue-derived mesenchymal stem cells.

The subject of the present invention may be a vertebrate, preferably a mammal, more preferably a rat, rabbit, guinea pig, hamster, dog, cat or human being, and most preferably a human being, but is not limited thereto.

The treatment of a subject with periodontal tissue-derived mesenchymal stem cells of the present invention may be a treatment performed one or more times, preferably a treatment performed three times or more at an interval of 1 to 3 weeks, and more preferably a treatment performed three or more times at an interval of 2 weeks.

Hereinafter, the present invention will be described in more detail through examples. These examples are only for illustrating the present invention in more detail, and it will be apparent to a person having ordinary skill in the pertinent art that the scope of the present invention is not limited by these examples without departing from the gist of the present invention. Statistical analysis was performed according to one-way ANOVA followed by Tukey's test using SPSS (SPSS Inc., Chicago, IL, USA). Results are presented as mean±standard error. When P<0.05, it was determined to be significant.

MODES FOR CARRYING OUT THE INVENTION

Example 1. Preparation of Periodontal Tissue-Derived Mesenchymal Stem Cells

All chemicals were purchased from SigmaAldrich® (St. Louis, MO, USA), and the medium was purchased from Gibco Life Technologies (Gaithersburg, MD, USA). In order to obtain the periodontal tissue-derived mesenchymal stem cells, the present inventors established a new freezing protocol, and named it a vitrification method. The method is designed to effectively preserve cells in a tissue by using a composition for vitrification of tissue containing ethylene glycol, sucrose and glucose, and is described in Korean Patent No. 10-1551900 (Patent Document 1), which is a related art of the present inventors, which is incorporated herein by reference in its entirety.

More specifically, the periodontal tissue that was discarded after being extracted from an impacted wisdom teeth patient around the age of 20 was provided by the Department of Oral and Maxillofacial Surgery at Gyeongsang National University Hospital. The tooth tissue was separated from the extracted wisdom teeth using a sterile scalpel and vitrified, and was stored for at least 3 months and then thawed. After thawing the freezing tube stored in liquid nitrogen in the water at 37° C. for 1 to 2 minutes when thawing the tissue, DPBS containing 100 U/ml of penicillin/streptomycin and 0.25 μg/ml of amphotericin B (Invitrogen) was used to completely remove a cryopreservative, and was washed several times by centrifugation at 1500 rpm for 5 minutes. In order to isolate mesenchymal stem cells from the periodontal tissue, collagenase type IV (Sigma, USA) was enzymatically treated for 30 minutes. The treated tissue was filtered once each in a 100 μm cell strainer (BD Falcon™, USA) and 40 μm cell strainer (BD Falcon™ USA), and then transferred to a 15 ml conical tube (15 ml polypropylene conical tube; BD Falcon™, USA) and then washed twice by centrifugation at 1500 rpm for 5 minutes using DPBS containing penicillin/streptomycin and amphotericin B (Gibco, USA).

In 25 T-flasks (Nunc™, Roskilde, Denmark) using 4 mL of DMEM (Dulbecco's modified Eagle's Medium) containing 10% fetal bovine serum (FBS), 1% L-glutamine (Glutamax™ and 1% penicillin/streptomycin), the vitrified periodontal tissue-derived mesenchymal stem cells were cultured in 5% $CO_2$, 37° C. and humid conditions. The medium was changed once every 3 days. Immediately before administration to the animals, 4 to 5 passages of cells were removed from the bottom of the culture container with 0.25% trypsin/EDTA and washed with DPBS. The isolated cells were counted using a hemocytometer, and $1 \times 10^6$ cells were diluted in 200 μl of cold DPBS and used for subsequent experiments (hereinafter referred to as MSCs).

Example 2. Production of Male Infertility Animal Model Through Intake of High-Fat Diet Forty 8-week-old male C57BL/6J mice weighing 20-22 g were purchased from Central Lab Animal Inc. (Seoul, Korea) and used. All mice were bred at a room temperature of 25±2° C. and humidity of 30-40% by maintaining a 12-hour light-dark cycle, and allowed free access to water and food. Mice were randomly divided into 4 groups:
1. Control group (Con) (n=10): normal diet for 10 weeks
2. HFD group (n=10): high-fat diet containing 60 kcal % fat for 10 weeks+intraperitoneal administration of 200 μl of PBS after 10 weeks
3. MSCi group (n=10): high-fat diet containing 60 kcal % fat for 10 weeks+after 5, 7, and 9 weeks of a high-fat diet, intraperitoneal administration of $1 \times 10^6/200$ μl of MSCs each
4. MSCs group (n=10): high-fat diet containing 60 kcal % fat for 10 weeks+after 8 weeks of a high-fat diet, intraperitoneal administration of $1 \times 10^6/200$ μl of MSCs for 5 consecutive days.

All mice were weighed weekly, and after 10 weeks, 0.5 μL/g of tiletamine-zolazepam (Zoletil®) and 0.5 μL/g of xylazine (Rompun, Bayer Korea Ltd., Seoul, Korea) were injected and sacrificed. The mouse blood was collected by cardiac puncture, and the residual blood was removed by perfusion with PBS containing heparin. Liver and testicular tissues were obtained and weighed for tissue weight/body weight calculation. All animal experiments were performed according to the guidelines for the treatment and use of laboratory animals of Gyeongsang National University. The results are shown in FIG. 1.

Figure 1A:
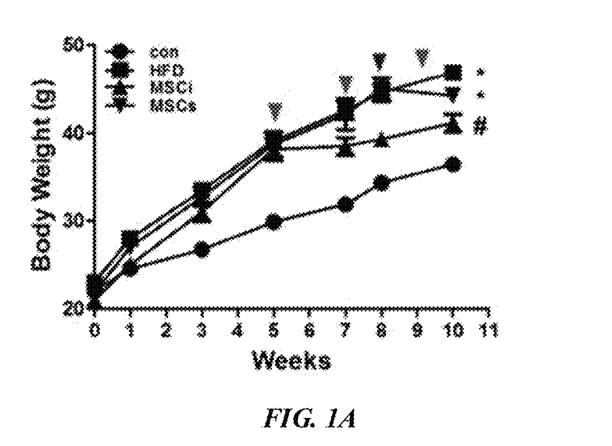
FIG. 1 shows the results of measuring the body weight (A), and liver (B) and testicular (C) tissue weights of mice in each experimental group induced by NAFLD and male infertility with a high-fat diet and a control group (*p<0.05, compared with the control group; #p<0.05, compared with the HFD group).
Figure 1B:
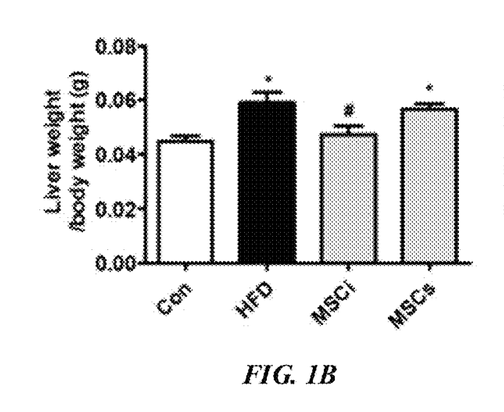
Figure 1C:
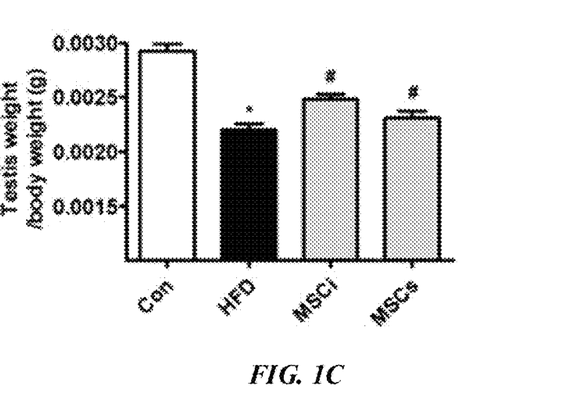

As shown in FIG. 1A, the body weight of the HFD group was significantly higher than that of the control group from the 3rd week of the high-fat diet (p<0.05). The body weight of the MSCi group was significantly lower than that of the HFD group at the first administration of MSCs (p<0.05). In the case of liver weight, as shown in FIG. 1B, the liver weight of the HFD group was significantly increased compared to the control group (p<0.05), and the MSCi group showed a significantly reduced liver weight compared to the HFD group (p<0.05). On the other hand, the MSCs group showed no significant difference compared with the HFD group. In addition, in the case of testicular weight, as shown in FIG. 1C, it was identified that the testicular weight of the HFD group was significantly reduced compared to the control group (p<0.05), and the testicular weight of both the MSCi and MSCs groups was significantly increased compared to the HFD group (p<0.05).

Example 3. Histological Analysis Before and After MSC Administration

In order to identify the therapeutic effect of periodontal tissue-derived mesenchymal stem cells on liver and testis, histological analysis was performed. Liver and testicular tissues were fixed in 4% formaldehyde, dehydrated, and then embedded in paraffin and cut into 5 μm thick sections. After removing the paraffin component from the tissue section using xylene, rehydration with ethanol was performed, and then staining with hematoxylin and eosin (H&E). After all the stained tissues were dehydrated, washed, and mounted with a permount (Fisher scientific, NH, USA), the degree of staining was checked with an optical microscope (Nikon Eclipse 80i) and Photo Imaging System (Canon 600D). Seminiferous tubule diameter and Leydig cell number were measured using NIS Elements BR3.2. A total of 150 seminiferous tubules were measured in 10 mice per group (3 fields per mouse, 5 seminiferous tubules randomly per field), and Leydig cells were counted in 30 captured images (3 fields per mouse, 10 mice). The results are shown in FIG. 2.

Figure 2A:
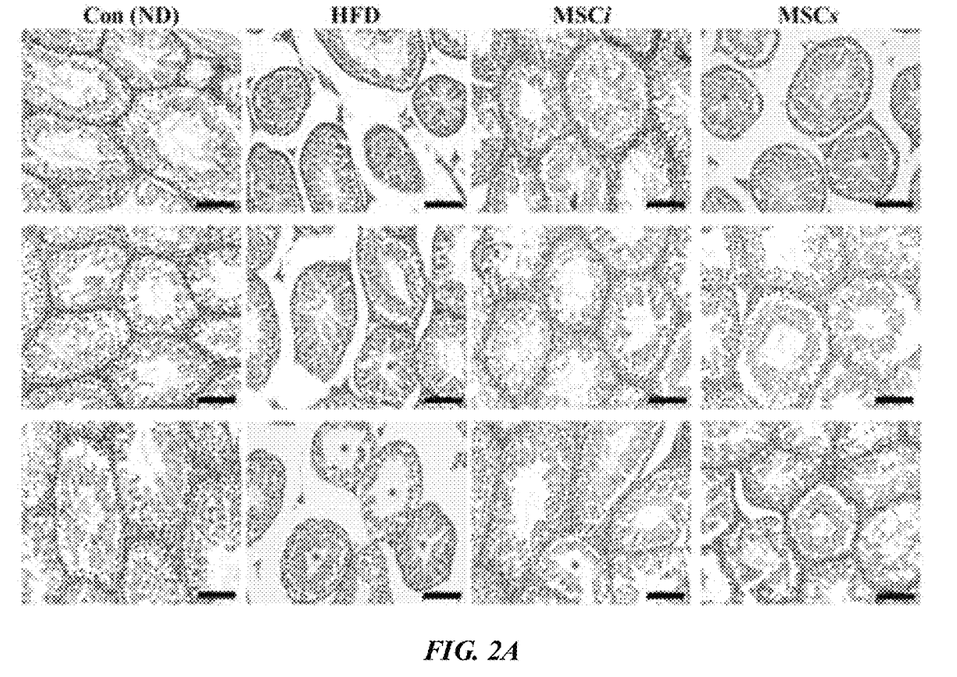
FIG. 2 shows the results of histological analysis of testicular tissue of mice in the control group and each experimental group, and the H&E staining results corresponding to each row show the histological findings of different mice, respectively (scale bar=100 μm, magnification=×200) (A). In addition, the results of measuring the diameter of the seminiferous tubules (B) and the number of Leydig cells (C) in the testicular tissue of the control group and each experimental group are shown (*p<0.05, compared with the control group; #p<0.05, compared with the HFD group).
Figure 2B:
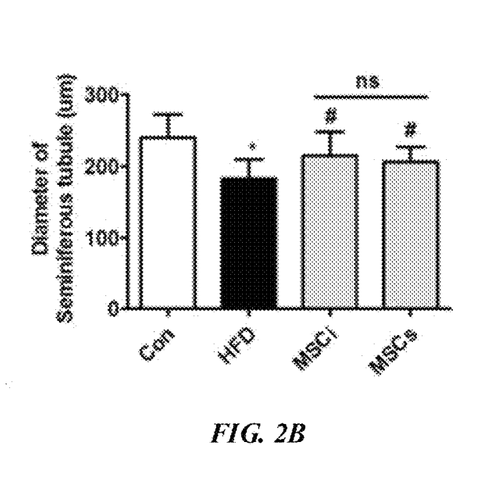
Figure 2C:
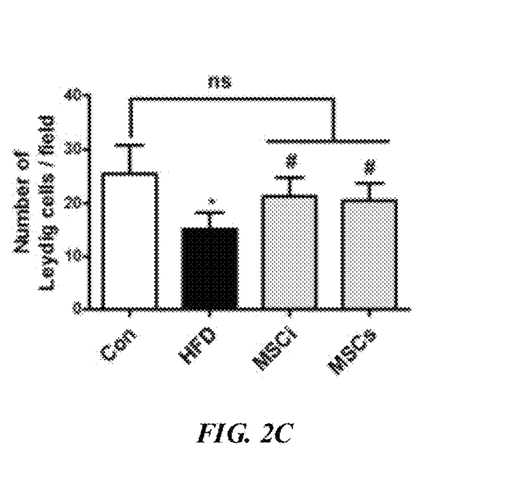

As shown in FIG. 2, it was identified that the control group showed normal testicular histological characteristics along with the observation of spermatogenesis in the seminiferous tubules, whereas in the HFD group, the size of the seminiferous tubules was smaller than that of the control group, and abnormal features such as a small number of spermatids in about 30% of the seminiferous tubules, no lumen, and no spermatogenesis in the lumen were observed. On the other hand, it was identified that the MSCs and MSCi groups showed improvement in the seminiferous tubules, such as the recovery of the testicular structure and the spermatogenesis in the lumen (A). In addition, in the case of the diameter of seminiferous tubules, the HFD group significantly decreased than the control group ($p<0.05$), and the diameter length increased in the MSCs and MSCi groups, thus identifying that the histological characteristics of the seminiferous tubules were remarkably recovered ($p<0.05$) (B). Furthermore, in the case of testosterone-producing Leydig cells, it was identified that the HFD group significantly decreased the number of cells than the control group ($p<0.05$), whereas the cell number significantly increased in the MSCi and MSCs groups ($p<0.05$) (C).

Through the above experimental results, it was identified that NAFLD and male infertility animal models in which testicular atrophy was induced by a high-fat diet were successfully prepared, and that the periodontal tissue-derived mesenchymal stem cells were effective in male infertility when administered. On the other hand, there was a slight difference in the treatment efficacy depending on the administration method. It was identified that at each time point after 5, 7, and 9 weeks of a high-fat diet, the MSCi group administered with mesenchymal stem cells showed a better therapeutic effect on body weight and seminiferous tubular recovery than the MSCs group administered with mesenchymal stem cells for 5 consecutive days after 8 weeks. In subsequent experiments, only the MSCi group was selected as the MSC group and the experiment was performed (hereinafter, referred to as the MSC group).

Example 4. Apoptosis Analysis According to MSC Administration

In order to evaluate apoptosis induced by a high-fat diet, TUNEL analysis was performed. The levels of apoptosis in liver and testicular tissues were evaluated using a TUNEL (terminal deoxynucleotidyl transferase-mediated dUTP nick end labeling) kit (TUNEL, Roche, IN, USA). Ten areas were randomly selected from each slide, and the number of brown-stained nuclei was counted as the number of TUNEL-positive cells under 400 magnifications, and the average of the measured numbers was calculated. All analyzes were performed blindly using NIS Elements BR3.2. The results are shown in FIG. 3.

Figure 3A:
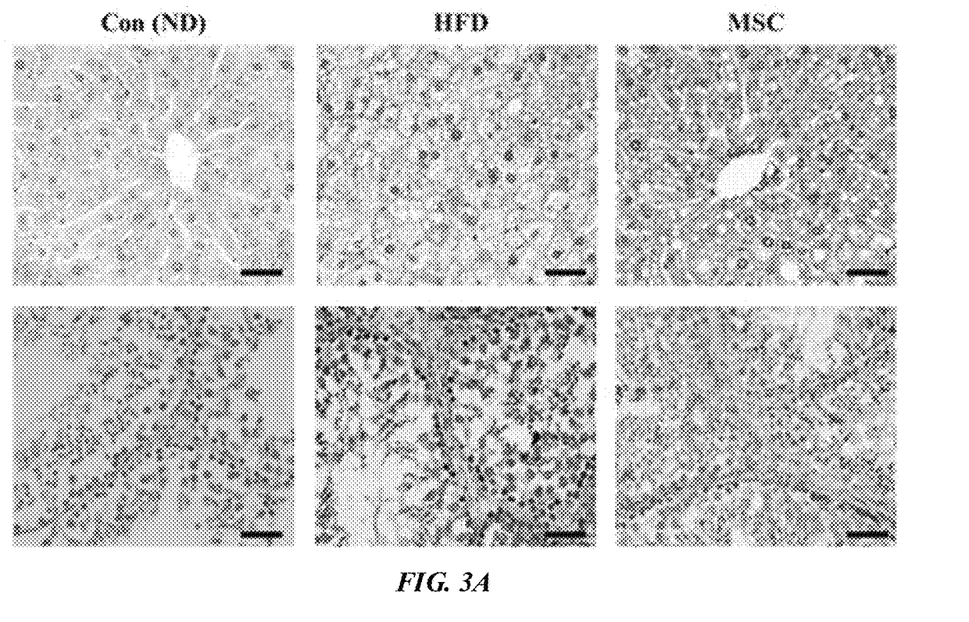
FIG. 3 shows the TUNEL analysis results for liver and testicular tissues of the control and experimental groups, each of which corresponds to a TUNEL staining result (A; scale bar=50 μm, magnification=×400), a TUNEL-positive cell (cell death) count result in liver tissue (B), and a TUNEL-positive cell count result in testicular tissue (C) (*p<0.05, compared with the control; #p<0.05, compared with the HFD group).
Figure 3B:
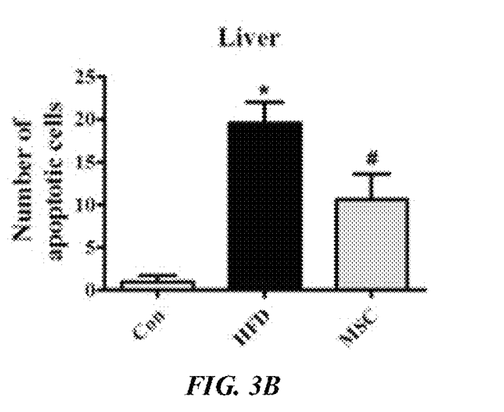
Figure 3C:
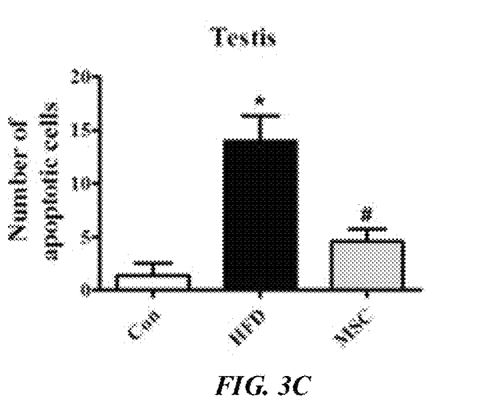
Figure 4A:
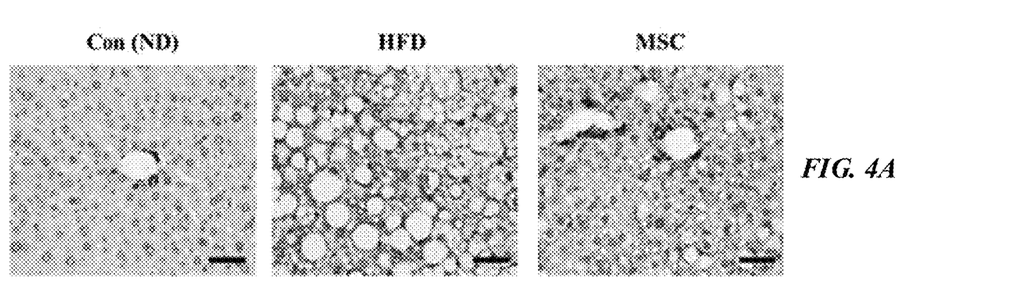
FIG. 4 shows the results of immunohistochemical analysis for identifying the activity of enzymes related to liver-specific estrogen metabolism, each of which corresponds to the aromatase expression level in each group (A; scale bar=50 μm), the expression level of CYP1A2 (B; scale bar=100 μm), and the ratio of the aromatase positive signal region in the total region (C) and the ratio of the CYP1A2 positive signal region in the total region (D) as a result of quantifying the expression level (*p<0.05, compared with the control group; #p<0.05, compared with the HFD group).
Figure 4B:
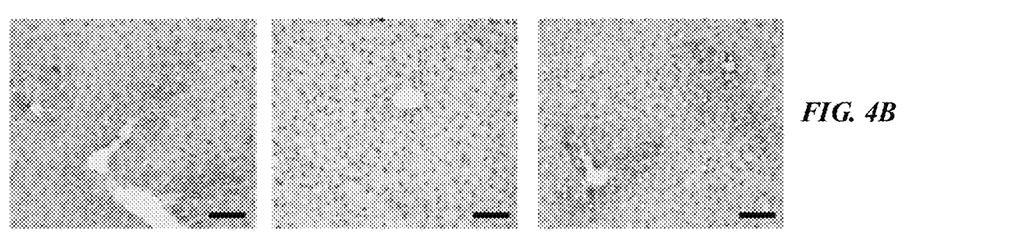
Figure 4C:
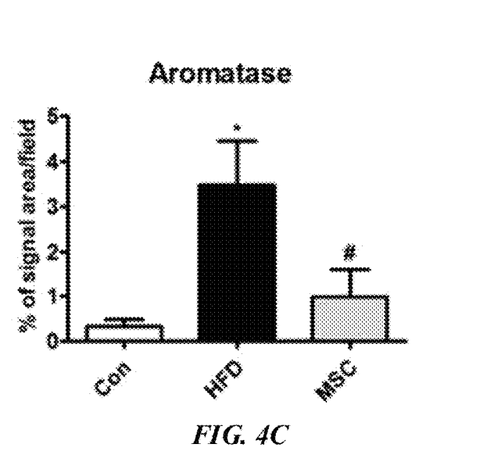
Figure 4D:
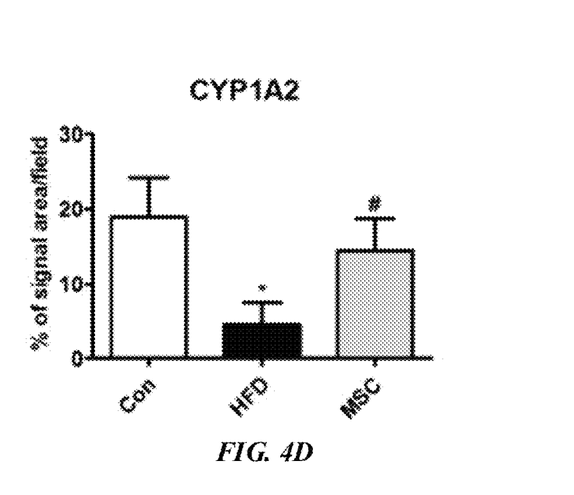

As shown in FIG. 3, it was identified that the brown-stained nuclei were significantly increased in the liver and testicular tissues of the HFD group, and significantly decreased in the MSC group administered with the periodontal tissue-derived mesenchymal stem cells. Through the above results, it was identified that apoptosis was significantly increased by a high-fat diet in both liver and testicular tissues ($p<0.05$), but apoptosis was significantly reduced by administration of mesenchymal stem cells ($p<0.05$).

Example 5. Changes in Liver Function According to MSC Administration

In order to evaluate changes in liver function related to estrogen metabolism in an animal model of male infertility, the expression levels of aromatase and CYP1A2 were analyzed by immunohistochemistry. For immunohistochemistry (IHC), rehydrated sections were boiled in 0.1 M citric acid buffer (pH 6.0) for 10 minutes to restore antigen, and endogenous peroxidase activity was blocked by reacting with 3% $H_2O_2$ at room temperature for 30 minutes. Tissue sections were reacted with ABP (LS-B12124, LSBio), monoclonal mouse anti-cytochrome P450 1A2, CYP1A2 (sc-53241, Santacruz), and polyclonal rabbit anti-aromatase (ab18995, Abcam) diluted 1:100 overnight at 4° C. Thereafter, a secondary antibody IgG (Vector Laboratories, Burlingame, CA, USA) diluted 1:200 and conjugated with biotin was applied, and then was reacted with ABC reagent (avidin-biotin-peroxidase complex; ABC Elite Kit, Vector Laboratories). All slides were color-developed with 0.05% diaminobenzidine tetrahydrochloride (DAB) (Sigma-Aldrich) and counterstained with Mayer's hematoxylin. Positive signals were analyzed in 30 fields per each group (3 random fields selected from 10 slides), and the ratio of positive signal area/all areas was calculated. The results are shown in FIGS. 4 and 5.

As shown in FIG. 4, it was identified that the level of aromatase expression in the HFD group was significantly increased as fat was accumulated in the liver parenchyma ($p<0.05$), whereas in the MSC group, as the hepatic steatosis improved, the expression level of aromatase was significantly reduced ($p<0.05$) (A and C). In addition, while CYP1A2, a major estrogen hydroxylase in the liver, was broadly expressed overall in the liver of the control group, its expression was dramatically reduced in the HFD group, and the expression of CYP1A2 was also significantly recovered in the MSC group as hepatic steatosis was improved (B and D). Through the above results, it was identified that the liver-specific estrogen metabolism was recovered by administering mesenchymal stem cells to the male infertile animal model, and hepatic steatosis was also improved in mice induced by a high-fat diet. The above results also suggest that estrogen metabolism is abnormal due to induction of hormonal imbalance in the HFD animal model.

Figure 5A:
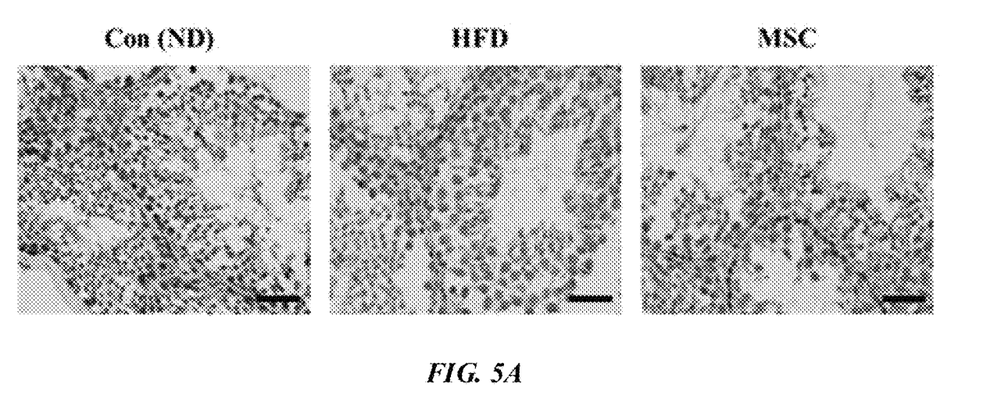
FIG. 5 shows the results of evaluating the function of Sertoli cells in the seminiferous tubules, each of which corresponds to the results of immunohistochemical staining identifying the expression of androgen binding protein (ABP) (A; scale bar=50 μm, magnification=×400), and the ratio of the ABP-positive signal region in the total region (B) as a result of quantifying the expression level (*p<0.05, compared with the control group; #p<0.05, compared with the HFD group).
Figure 5B:
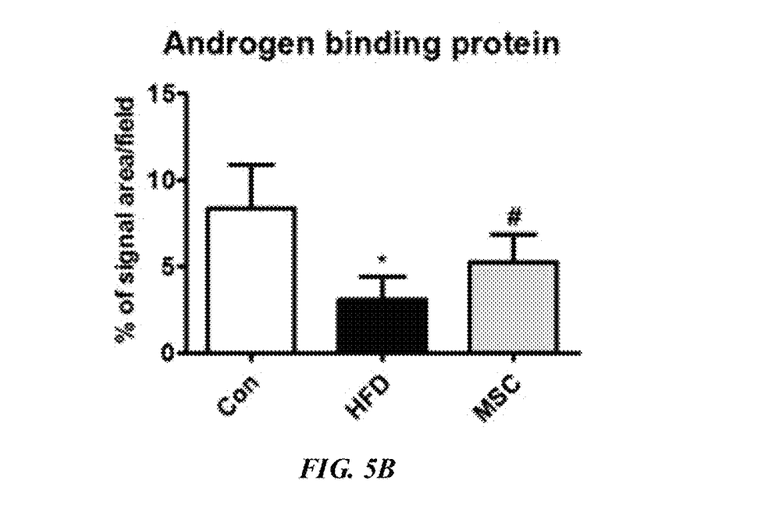

Furthermore, as shown in FIG. 5, it was identified that androgen binding protein (ABP) secreted from Sertoli cells in the seminiferous tubules was highly expressed in the basement membrane of the seminiferous tubules of the control group, whereas in the HFD group, the expression was significantly reduced without structural change or loss of Sertoli cells ($p<0.05$). On the other hand, it was identified that when the mesenchymal stem cells were administered, the expression of ABP was significantly increased. From the above results, it was identified that the low level of ABP was not due to the loss of Sertoli cells, but was due to a hormonal abnormality due to liver tissue damage induced by a high-fat diet.

Example 6. Improvement Effect of Sex Hormone Imbalance According to MSC Administration Mouse blood was collected by cardiac puncture by the method described in Example 2, and serum was collected by centrifugation at 400×G for 10 minutes and stored at −80° C. until use. In order to identify whether periodontal tissue-derived mesenchymal stem cells can improve the sex hormone imbalance induced by a high-fat diet and NALFD, testosterone in mouse serum (T; ADI-900-065, ENZO), 17(3-estradiol (E2; ADI-900-174, ENZO), FSH (LS-F39325, LSBio), LH (LSF22503, LSBio), TNF-α (ADI-900-047, ENZO), and IL-1β were analyzed by ELISA. The results are shown in FIG. 6.

As shown in FIG. 6, it was identified that the testosterone level was significantly decreased in the HFD group (p<0.05), but significantly increased after MSC administration (p<0.05) (A). In the case of 17β-estradiol converted from testosterone by aromatase, the level was significantly increased in the HFD group (B), and the testosterone/17β-estradiol value, which is a clinical indicator of sex hormone balance, was significantly increased after MSC administration (p<0.05) (C). Through the above results, it was identified that sex hormone imbalance could be induced in a high-fat diet animal model, which could be treated through the administration of mesenchymal stem cells.

Figure 6A:
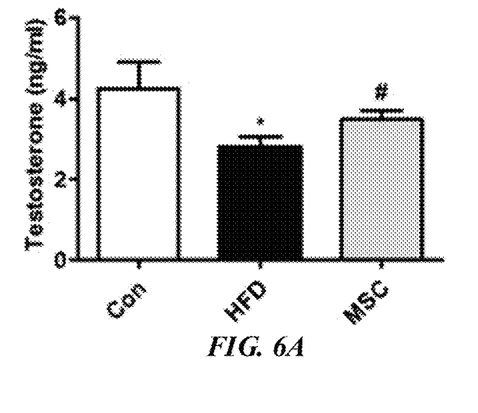
FIG. 6 shows the results of analyzing the serum hormone levels related to the hypothalamus-pituitary-gonad axis (HPG axis) related to fertility (*p<0.05, compared with the control group; #p<0.05, compared with the HFD group).
Figure 6B:
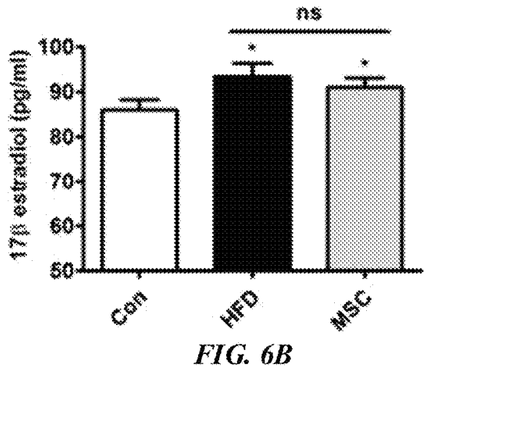
Figure 6C:
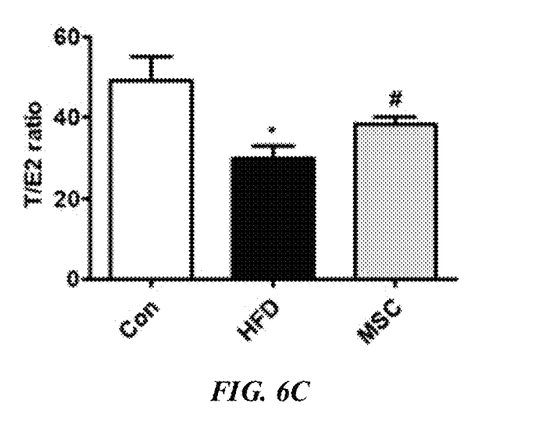
Figure 6D:
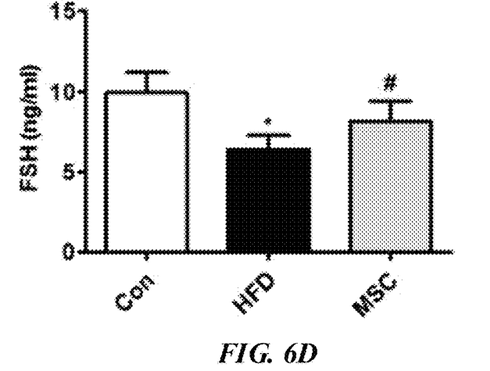
Figure 6E:
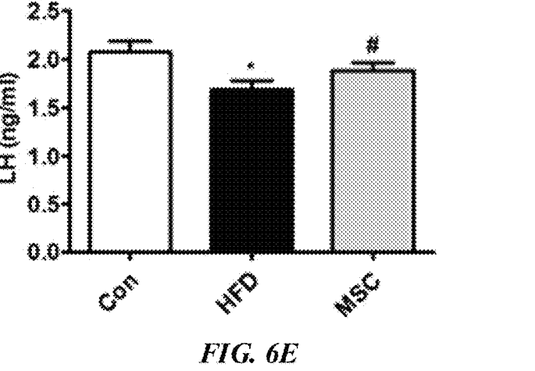

Furthermore, as a result of measuring FSH and LH levels that stimulate the testes to produce ABP and testosterone to identify male hypogonadism, it was identified that both gonadotropins were significantly decreased in the HFD group, but increased significantly after MSC administration (D and E). Through the above results, it was identified that the decrease in ABP production was affected by the decrease in FSH caused by sex hormone imbalance.

Figure 7:
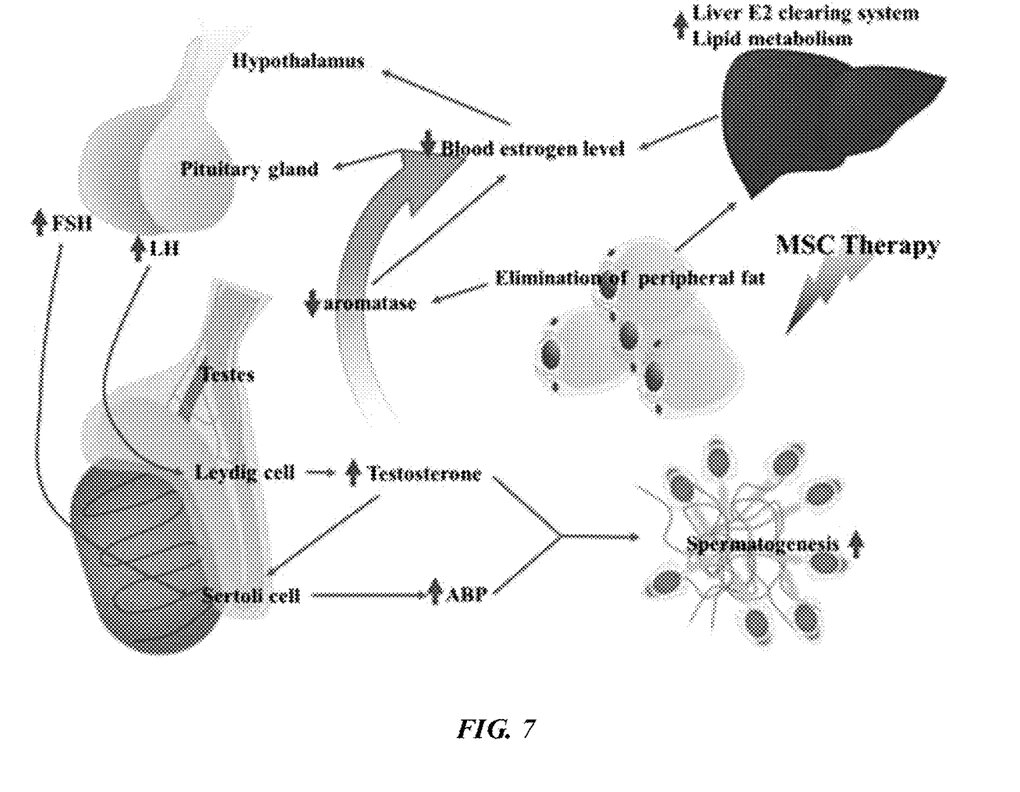
FIG. 7 is a diagram showing the mechanism of action (Mode of Action, MoA) of the treatment of periodontal tissue-derived mesenchymal stem cells against male hypogonadism induced by NALFD. The periodontal tissue-derived mesenchymal stem cells according to the present invention may alleviate male infertility including male hypogonadism induced by NALFD by improving estrogen metabolism and lipid homeostasis in the liver.

The mechanism of action (Mode of Action, MoA) for treatment of male infertility of the periodontal tissue-derived mesenchymal stem cells of the present invention identified in the above Examples is shown in FIG. 7.

Among the various animal models of inducing NAFLD, it is reported that the high-fat diet animal model has the pathological characteristics most similar to that of human NAFLD, and exhibits similar physiological changes such as weight gain, increased blood sugar, and increased metabolic disease.

The present inventors prepared an animal model induced by a high-fat diet in order to develop a new therapeutic agent for male infertility that can appear in men with obesity or NAFLD, and identified that when administered to the animal model with periodontal tissue-derived mesenchymal stem cells, the histological characteristics of the seminiferous tubules were restored, sex hormone imbalance was alleviated, various hormone metabolizing enzymes was expressed, and histological findings were normalized through fat metabolism and hepatocyte recovery.

Moreover, the periodontal tissue-derived mesenchymal stem cells which are an active ingredient in the present invention may be obtained in the most non-invasive manner and as such, are expected to be advantageously used as a cell therapeutic agent for male infertility.

From the foregoing, the specific portions of the present invention have been described in detail. Therefore, it is apparent to a person having ordinary skill in the pertinent art that such specific technology is merely a preferable embodiment, and the scope of the present invention is not limited thereto. Accordingly, the substantial scope of the present invention is defined by the appended claims and their equivalents.

The invention claimed is:

1. A method for treating male infertility in a subject in need thereof, the method comprising administering to the subject a therapeutically effective amount of a pharmaceutical composition comprising periodontal tissue-derived mesenchymal stem cells.

2. The method of claim 1, wherein the pharmaceutical composition is administered three times or more at an interval of 1 to 3 weeks.

3. The method of claim 1, wherein the pharmaceutical composition is administered at a dose effective to deliver about $10^4$ to about $10^{10}$ periodontal tissue-derived mesenchymal stem cells to the subject.

4. A method for treating male infertility in a subject in need thereof, the method comprising administering to the subject a therapeutically effective amount of a therapeutic agent comprising periodontal tissue-derived mesenchymal stem cells.

5. The method of claim 4, wherein the therapeutic agent is administered three times or more at an interval of 1 to 3 weeks.

6. The method of claim 4, wherein the therapeutic agent is administered at a dose effective to deliver about $10^4$ to about $10^{10}$ periodontal tissue-derived mesenchymal stem cells to the subject.

* * * * *